United States Patent [19]
Branemark et al.

[11] Patent Number: 4,781,694
[45] Date of Patent: Nov. 1, 1988

[54] ABDOMINAL WALL PATHWAY

[76] Inventors: Per-Ingvar Branemark, Ändergatan 3, S-431 39 Mölndal; Jarl Almén, Fornborgsvägen 13, S-436 00 Askim; Lars-Magnus Bjursten, Linnégatan 9, S-413 09 Göteborg; Peter Thomsen, Ättehösgatan 10B, S-416 74 Göteborg; Lars E. Ericsson, Brunörtevägen 7, S-438 00 Landvetter, all of Sweden

[21] Appl. No.: 832,787
[22] Filed: Feb. 26, 1986
[30] Foreign Application Priority Data
Feb. 27, 1985 [SE] Sweden .............................. 8500946
[51] Int. Cl.$^4$ .............................................. A61M 5/00
[52] U.S. Cl. .................................. 604/175; 128/334 C
[58] Field of Search ................ 604/175, 8; 128/334 C
[56] References Cited

U.S. PATENT DOCUMENTS

| 3,540,451 | 11/1970 | Zeman .................... 604/175 X |
| 3,663,965 | 5/1972 | Lee, Jr. et al. ................. 3/1 |
| 3,752,162 | 8/1973 | Newash ..................... 128/348 |
| 4,344,435 | 8/1982 | Aubin ...................... 604/175 |
| 4,375,816 | 3/1983 | Labianca ..................... 604/8 |
| 4,405,319 | 9/1983 | Cosentino .................. 604/175 |
| 4,496,349 | 1/1985 | Cosentino .................. 604/175 |
| 4,634,422 | 1/1987 | Kantrowitz et al. ......... 604/175 X |

FOREIGN PATENT DOCUMENTS

0102342A2 of 0000 European Pat. Off. .
0078565A1 of 0000 European Pat. Off. .
2056282A of 0000 United Kingdom .

Primary Examiner—Dalton L. Truluck
Attorney, Agent, or Firm—Pollock, Vande Sande & Priddy

[57] ABSTRACT

The present invention relates to a device for providing a permanent pathway between the abdominal cavity and/or organ located in the abdominal cavity and the exterior of the body. The device is made of commercially pure titanium or at least coated with titanium on the surfaces which directly contact the abdominal wall tissue. The device comprises a first anchorage portion, designed for implantation into the connective tissue of the abdomen during the first operation, a covering screw with plug for blocking of the central opening in the anchorage portion during the healing phase and a skin penetration portion in the form of a titanium tube for connection to the anchorage portion during the second operation after prior removal of the covering screw with plug.

10 Claims, 5 Drawing Sheets

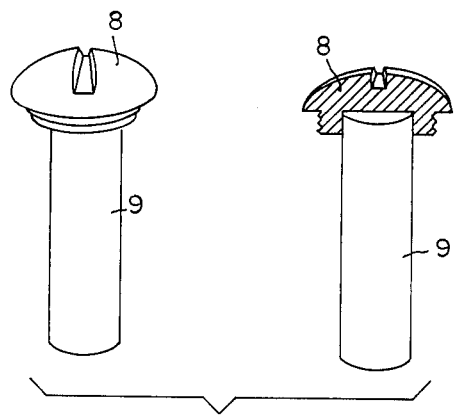
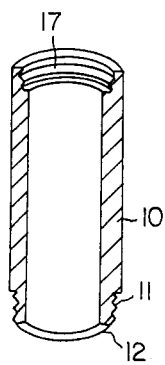
FIG. 4      FIG. 5
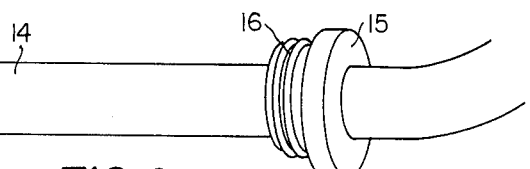
FIG. 6
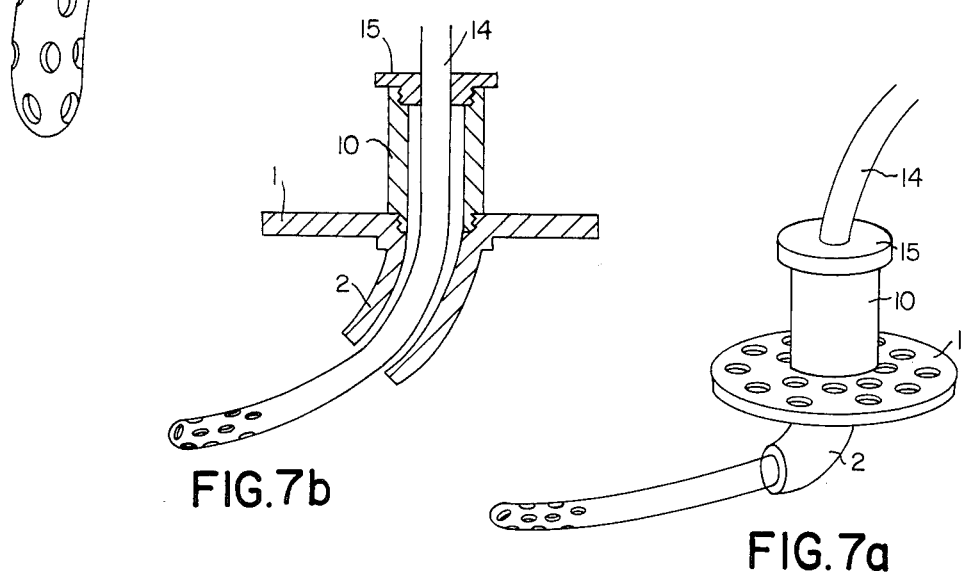
FIG. 7b      FIG. 7a

ABDOMINAL WALL PATHWAY

BACKGROUND OF THE INVENTION

The present invention relates to a device for establishment of a permanent pathway between the abdominal cavity or an organ situated in the abdominal cavity and the exterior of the body to permit for example chronic peritoneal dialysis or other forms of treatment of the abdominal cavity or organs situated therein.

Every year, some 55-60 patients per million inhabitants in Sweden encounter chronic kidney failure. As a rule, the failure is a relatively slowly progressing condition requiring active uremic treatment, ie dialysis treatment and/or kidney transplantation. During the 1960s and 1970s haemodialysis has been the predominant form of treatment, while peritoneal dialysis has been a second-choice alternative on account of the practical problems encountered.

In 1978, however, the foundation was laid, both practically and theoretically, for so-called continuous peritoneal dialysis (CAPD) and since then technical developments have made CAPD increasing popular. A survey of the number of dialysis patients in Sweden conducted on 18 Sept. 1984 revealed that a total of 1 071 patients were being treated with some kind of dialysis. Of these, 221 were being treated with chronic peritoneal dialysis. The corresponding figure for Europe as of 31 Dec., 1983, shows that 60 691 patients were receiving haemodialysis and haemofiltration treatment, while 5 385 patients were being treated with peritoneal dialysis.

When the CAPD treatment was first introduced, it was found that infections in the abdominal cavity, so-called peritonitis, were far more common with CAPD treatment than with the otherwise normally used intermittent peritoneal dialysis treatment. The CAPD treatment has several clinical and laboratory advantages in comparison with the haemodialysis treatment. Provided that further development takes place on the technical side, increasing interest in CAPD as a form of treatment may be anticipated. Hitherto, this technical development has largely been concentrated on the connection between dialysis solution, usually supplied in 2-liter disposable plastic bags, and the catheter in the patient's abdominal cavity. Various disinfection routines have reduced the risk for contamination due to handling of the system by the patient. Since 1978, this technical development has resulted in a reduced frequency of peritonitis to the current level of around 1 peritonitis per 8 patient observation months. The bacteria staphylococcus epidermidis normally present on the skin is the commonest cause of peritonitis. A major share of the cases of peritonitis however can not be attributed to technical handling of the equipment but has some other origin.

Another clinically highly important complication is the so-called tunnel infection around the inserted peritoneal dialysis catheter. Due to the fact that the technique and materials currently used often cause a rejection phenomena with a tunnel or recess formation adjacent to the catheter, a serious infection often arises. These tunnel infections, often caused by staphylococcus aureus in some instances, cause peritonitis.

SUMMARY OF THE INVENTION

The object of the present invention is to establish an abdominal wall pathway which allows the skin to retain the capability to resist bacteria in the pathway vicinity so that the occurrence of tunnel infections and peritonitis due to an incomplete infection defence around the abdominal wall pathway are eliminated to the greatest possible extent.

In this context, interest has been concentrated on the choice of material for the components included in the abdominal wall pathway and also in the surgical technique. Nowadays, CAPD is usually performed with a permanently implanted, operatively installed silicone catheter with two dacron cuffs which are sewn on close to the peritoneum and subcutis respectively. Such an installation gives rise to frequent problems, particularly infections at the point of exit from the skin (staph epidermis and staph aureus). Formation of adhesive bands is a minor problem in adequate dialysis technique.

It is previously known to permanently anchor oral and extra oral prostheses in bone tissue. To prevent loosening, a direct contact is desired, for example, an exact adaption between prosthesis and bone tissue. An exact adaption of this kind is referred to as osseointegration. The only implant that hitherto has been demonstrated in clinical praxis to remain anchored via direct contact between bone and implant, osseointegration, is in fact the Brånemark jaw-bone anchored dental bridge. The anchorage thereof is based on, among other things, the anchorage portion being of commercially pure titanium. The osseointegration principle developed by professor Brånemark and his colleagues has been used clinically for 20 years with good results and has been described in for example > P-I Brånemark et alia, "Osseointegrated fixtures in the treatment of endentuolousness Blomaterials, 1983, Vol 4, January and Rickard Shalak, "Biomechanical considerations in osseointegrated prostheses", The Journal of Prosthetic Dentistry, June 1983, Volume 49, Number 6.

Experiments have now illustrated (see below) that titanium is also accepted well by the tissue which lines the inside of the abdominal wall (peritoneum). The present invention exploits this circumstance and is characterized in its most general form in that the pathway is made of commercially pure titanium or at least coated with titanium on the surfaces which come into direct contact with abdominal wall tissue.

The so-called osseointegration principle, however, is not based solely on the implant being made of pure titanium, but also on an atraumic insertion technique of the anchorage portion of the titanium implant in a first operation, an unloaded healing-in phase of critical duration and a secondary operation with connection of a load imposing portion (the prosthesis part), ie a two-seance procedure with an interposed unloaded healing period.

In a preferred embodiment of the present invention the two-seance procedure is utilized in that the abdominal wall pathway comprises two main portions, partly a portion arranged to be implanted in the tissue of the abdomen and penetrating peritoneum at a first operation so that it remains in an unloaded condition during a healing phase during which the abdominal wall pathway is not taken into use and partly a second portion, the skin passage part, arranged to be connected to the first portion at a second operation after the healing phase.

BRIEF DESCRIPTION OF THE DRAWINGS

The invention will now be described in greater detail below with reference to the accompanying Drawings, wherein FIG. 4 shows the covering screw (plug) which is intalled during the healing phase, FIG. 5 shows the second, skin-penetrating portion in the form of a titanium tube, FIG. 6 shows the modified CAPD catheter which is connected to the abdominal wall pathway, FIG. 7 shows the device complete with the modified peritoneal catheter, in perspective (FIG. 7a) and in cross-section (FIG. 7b)

DESCRIPTION OF THE PREFERRED EMBODIMENTS

As mentioned above, the present invention is based on the establishment of a permanent anchorage between the abdominal wall tissue and the pathway where the aforesaid complications (tunnel infections, peritonitis) have been eliminated to the greatest possible extent. To permit such a permanent, tissue-compatible anchorage the device is made of pure titanium, or at least coated with titanium on the surfaces which come into direct contact with the tissue.

To ensure sucessful results from implants in bone tissue it is essential for the implant to have time to heal in before being subjected to load, see for example Albrektsson T., Brånemark P-I, Hansson H A and Lindström J.: "Osseointegrate titanium implant. Requirements for ensuring a long-last direct bone anchorage in man". Acta Ortop. Scand 52, 155-170, 1981.

The two-seance procedure as such is thus already known and will therefore not be more closely described here. What is new for the present invention, however, is that the implant of titanium is surgically inserted into a different type of tissue, namely that in the abdominal wall, and that the implant is then adapted to the special requirements imposed on an abdominal wall pathway.

The examples which will be described in the following are thus all adapted to the two-seance procedure. In its most general form, however, the invention is not limited to such a procedure but is characterized in that the pathway is made of commercially pure titanium. This choice of material should by itself give a definite reduction of the previously mentioned complications.

In a preferred embodiment of the present invention, healing-in of the device takes place in two stages so that it heals in the connective abdominal tissue and in the limitation of the abdominal cavity (peritoenum), the actual passage through the skin being made only after the healing in period and only in conjunction with this is the device taken into use.

The device therefore comprises two main portions, partly a first portion which is anchored in the abdominal tissue at the first operation and partly a second, skin-penetrating portion which is connected only at the second operation.

Figure 1A:
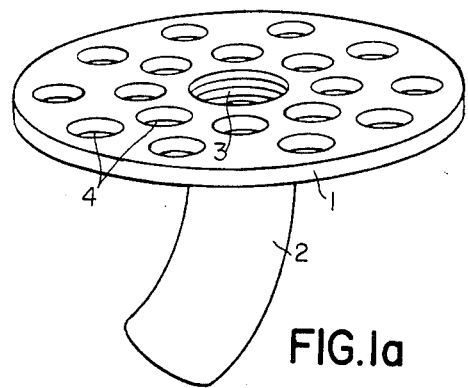
FIG. 1 shows schematically an embodiment of the first portion of the pathway in perspective (FIG. 1a) and in cross-section (FIG. 1b)
Figure 1B:
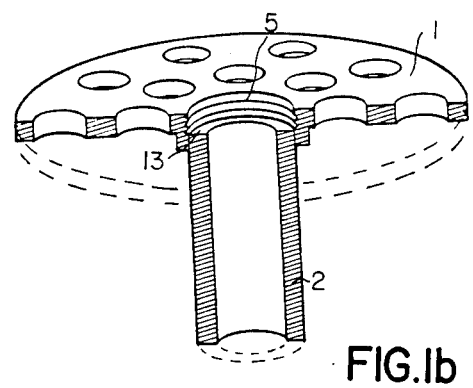
Figure 2:
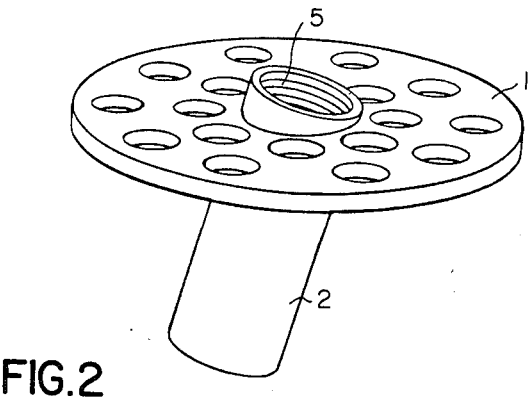
FIG. 2 shows an alternative embodiment of the first portion.
Figure 3:
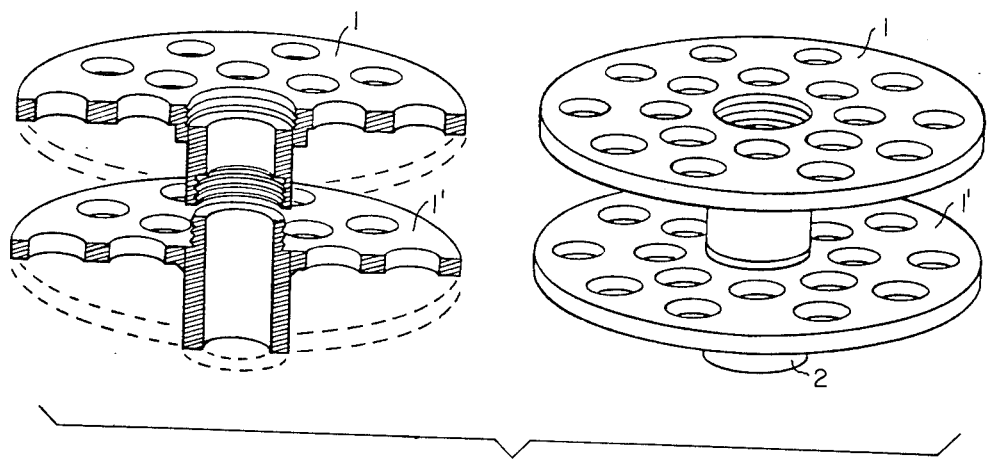
FIG. 3 shows a third embodiment of the first portion.

Different examples of how the first portion, the anchorage portion, can be designed are illustrated in FIGS. 1-3. A feature common to all the different embodiments is that the portion comprises a circular or oval plate or flange 1 intended to form the healing surface against the surrounding tissue in the abdominal cavity and a cylindrical pathway tube 2 to the abdominal cavity permanently united with the flange. The pathway tube has such a diameter that a conventional peritoneal catheter can be introduced into it through the central catheter opening 3 in the flange and through the tube. The flange 1 is provided with a plurality of through-going apertures 4 distributed across its surface. The portion is anchored securely and permanently through ingrowth of tissue in these apertures.

For anatomical reasons the pathway tube 2 penetrating into the abdominal cavity is slightly curved, see FIG. 1a, or an obliquely secured straight tube, see FIG. 2. The central catheter opening 3 and pathway tube 2 respectively, see FIG. 2, are provided with an internal screw thread 5 or some other locking device to permit connection of a covering screw or plug during the healing in phase and the second, skin-penetrating portion at the subsequent operation (see below).

The embodiment illustrated in FIG. 3 comprises two twinflanges 1, 1', arranged in two parallel planes so that a central pathway tube 2 for a catheter is formed. This embodiment is particularly useful for passages through thicker abdominal wall muscles and/or when improved anchorage is desired to through contact of a flange against both the inner and the outer tissue surface.

The first portion is entirely made of or, at least coated with commercially pure titanium with, an oxidized surface and a surface structure which is already known in connection with jaw bone fixtures. See for example Swedish Pat. No. 7902035-0.

The first portion is thus intended to be surgically implanted into the connective tissue 6 of the abdomen and in the limitation of the abdominal cavity (peritoneum) 7 in the vicinity of or in linea alba below the navel, see FIG. 8, and is allowed to heal-in during a healing period of 3-4 weeks during which period the pathway is not in use. At this first operation the catheter opening 3 is covered by a cover screw 8 with a plug 9 of silicone rubber or similar material, see FIG. 4. After the first operation, the incision in the skin is sewn together and the implant remains unloaded during the healing-in period.

In a second operation, performed some 4 weeks later, the tissue integrated operation site is opened and the cover screw with plug is removed from the now healed-in first portion and replaced with a skin-penetrating tube 10 of titanium ("chimney"), see FIG. 5. The lower portion of this tube is provided with a screw thread 11 which corresponds to the screw thread 5 in the first portion. The tube 10 is screwed in until its circular end surface 12 rests against the shoulder 13 of the first portion. The inside diameter of the titanium tube corresponds to the inside diameter of the pathway tube 2. After connection of a modified now clinically used CAPD catheter the device is ready to be used. A modified catheter of this kind is illustrated in FIG. 6. It consists of a conventional silicone rubber hose 14, but instead of the felt-like dacron cuffs which are used on present-day catheters a titanium cuff 15 has been glued onto the silicone hose. The titanium cuff is fitted with a thread 16 and screwed down into a female thread 17 in the upper portion of the titanium tube. The complete device with CAPD catheter is illustrated in FIG. 7.

Shown in FIG. 8 is how the device is installed in the abdominal wall through a two-seance procedure. FIGS. 8a and 8b show the first operation and FIGS. 8c–8f show the second operation. Schematically, the abdominal wall consists of skin (cutis+subcutis) 18, connective tissue 6, musculature 6a and peritoneum 7. During the first operation an incision is made in the skin 18, the skin flaps are folded aside and the first portion is anchored in the connective tissue 6 so that a pathway is formed through the tissue and peritoneum 7 into the abdominal cavity 19. The flange rests against the outer surface 20 or the connective tissue. At this first operation, the catheter opening is covered by a cover screw which is screwed into the pathway tube (FIG. 8a). The operation incision in the skin is then sewn together (FIG. 8b) and the healing-in period commences.

Figures 8A, 8B:
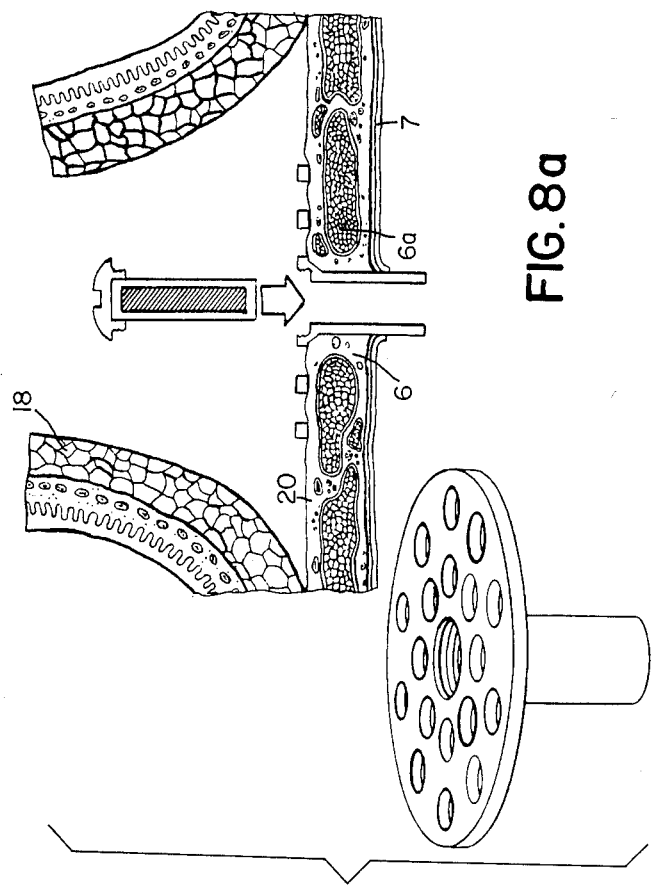
FIG. 8 shows how the device is installed in the abdominal wall through a two-seance procedure, FIGS. 8a and 8b showing the first operation and FIGS. 8c-8f the second operation.
Figure 8D:
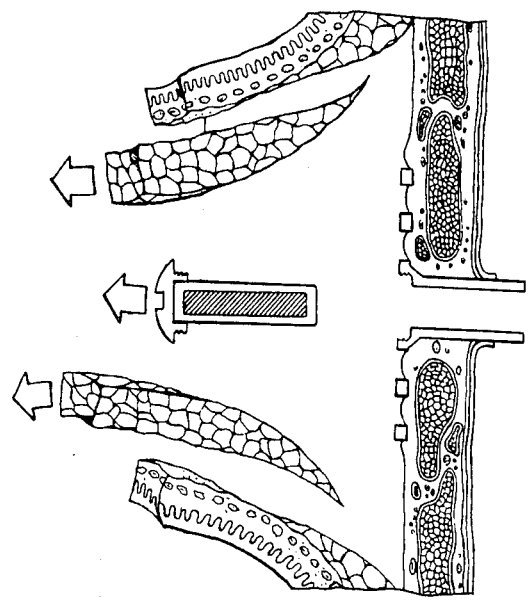
Figure 8C:
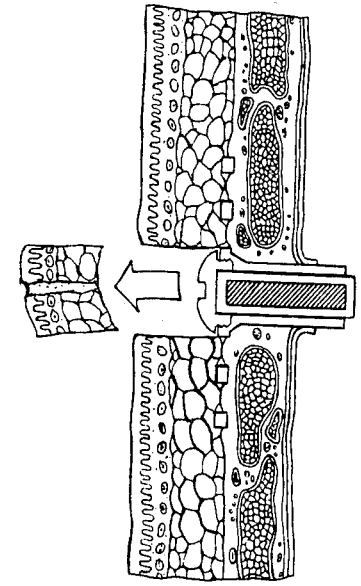
Figure 8F:
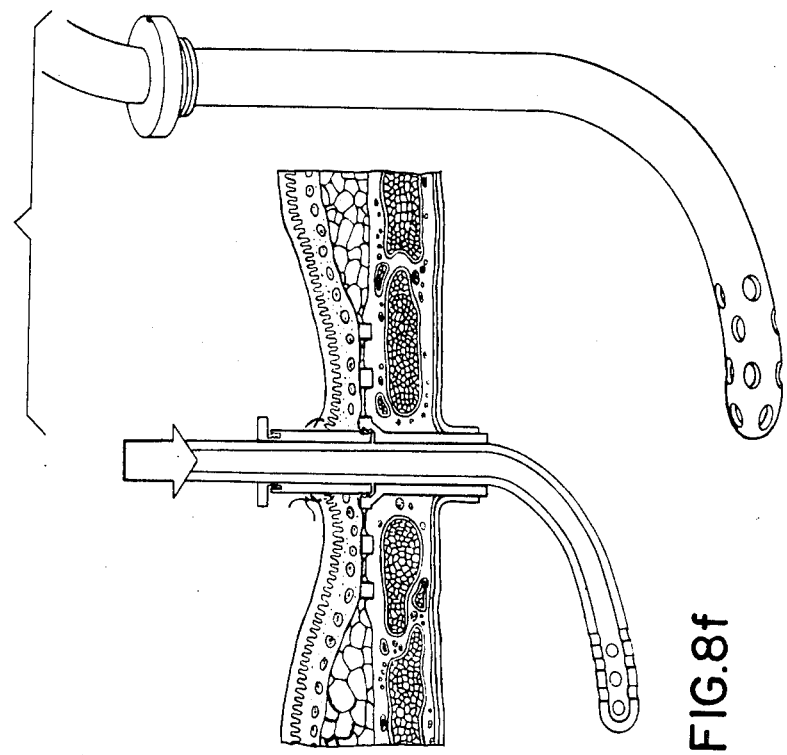
Figure 8E:
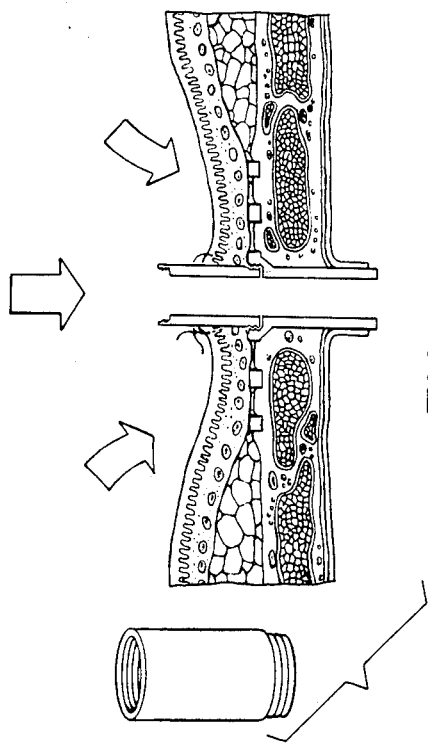

During the second operation, performed some 4 weeks later, the operation site (FIG. 8c) is opened and the covering screw with its plug is removed from the now healed-on first portion (FIG. 8d). In conjunction therewith some trimming of cutis 18 is also performed. In FIG. 8e the skin-penetrating tube is connected, the operation incision is sealed around the tube and the CAPD catheter is connected (FIG. 8f) whereupon the device is ready for use.

It should also be mentioned that experiments with titanium implants surgically inserted into the abdominal wall of rats (Sprange-Dawley) have verified that experience from the jaw reconstruction process can be applied to surgical insertion of titanium implants in the soft tissue of the abdominal wall. Titanium is well accepted by the tissue which lines the inside of the abdominal wall (peritoneum). In this context, reference should be made to Thomsen P., Bjursten L-M and Ericsson L-E: Titanium implants in the abdominal wall of the rat, abstract, src Biomat, res, San Diego, April 1985.

In the foregoing, the present invention has been described in connection with chronic peritoneal dialysis. It will be realized, however, that the invention is not confined to this case but can be varied within the scope of the subsequent patent claims.

We claim:

1. A device for providing a permanent pathway between the abdominal cavity and the exterior of the body comprising:
    a first anchoring means for implantation in the connective tissue of the abdomen during a first operation, and retained for a healing phase to allow ingrowth of said connective tissue, said first anchoring means including at least one plate member forming a healing surface against surrounding connective tissue and a tube extending downwardly from said plate member and in communication with a central through opening in said plate member for forming a pathway through the connective tissue and peritoneum wall into the abdominal cavity, said first anchoring means being capable of receiving a removable covering means for retention during said healing phase;
    a second skin penetration means for providing a pathway between said first means and the exterior of the body, said second means connectable to said first means during a subsequent second operation after said healing phase;
    said first and second means together forming said permanent pathway between said exterior of the body and the abdominal cavity for admitting medical devices into said cavity;
    wherein said first and second means are at least coated with titanium on surfaces coming into direct contact with the connective tissue.

2. A device as claimed in claim 1, wherein said plate member is further provided with a plurality of through-going apertures distributed across its surface for improvement of the anchorage stability.

3. A device as claimed in claim 1 wherein a covering means to be connected to said first means during said first operation for retention during said healing phase comprises a covering screw with a cylindrical plug of silicone rubber for blocking said central opening.

4. A device as claimed in claim 1 wherein said first means is provided with a corresponding internal screw thread for receiving said covering screw.

5. A device as claimed in claim 1 wherein said second means comprises a titanium tube.

6. A device as claimed in claim 5 wherein said titanium tube is provided with an external screw thread for screwing on said tube into said central opening of said first means.

7. A method for providing a permanent pathway between the abdominal cavity and the exterior of the body comprising the steps of:
    implanting a first anchoring means through the connective tissue of the abdomen and peritoneum wall during a first operation, said implanting step including:
    positioning a substantially flat plate-like titanium coated surface in close contact with the connective tissue and penetrating the connective tissue with a titanium coated cylinder forming a communication pathway through the connective tissue into the abdominal cavity;
    retaining said first means unloaded during a healing phase to allow tissue ingrowth;
    inserting a second titanium coated skin-penetration means for providing a pathway between said first means and the exterior of the body during a subsequent second operation after said healing phase;
    connecting said second means to said first means, thereby forming said permanent pathway between said exterior of the body and the abdominal cavity for admitting medical devices into said cavity.

8. A method according to claim 7 further comprising a step of providing a covering means into said first means and retaining said covering means for protection of said first means during said healing phase.

9. A method according to claim 8 further comprising a step of removing said covering means after said healing phase and before said second operation.

10. A method for installation of a device for establishing a permanent pathway between the peritoneum cavity and the exterior of the body comprising the steps of:
    installing a first portion of the device during a first operation and connecting a second portion of said device during a subsequent second operation, said first and second portion at least being coated with titanium on surfaces coming into direct contact with tissue;
    said first operation including the steps of:
    cutting an incision through the epidermis and skin,
    folding aside the skin flaps, anchoring said first portion into the connective tissue to form a pathway between a surface of the connective tissue and into said peritoneum cavity, said anchoring step including:

positioning a substantially flat disc-like part of said first portion against the connective tissue and penetrating the connective tissue and peritoneum with a tube extending downwardly to the peritoneum cavity; said tube being integral with said disc-like part and in communication with a central opening in said disc-like part;

covering said pathway in said first portion with covering means;

sewing the incision in the skin;

retaining said first portion with said covering means for a healing period to allow tissue ingrowth;

said second operation comprising the steps of:

opening said first operation site;

removing said covering means from said first portion; and connecting the second skin penetrating portion into said first portion, thereby forming said permanent pathway between the exterior of the body and the abdominal cavity for admitting medical devices into said cavity.

* * * * *